United States Patent
Ludemann-Hombourger et al.

(10) Patent No.: US 11,702,445 B2
(45) Date of Patent: Jul. 18, 2023

(54) AUTOMATED SYNTHESIS REACTOR SYSTEM WITH A RECIRCULATION LOOP

(71) Applicant: POLYPEPTIDE LABORATOIRES FRANCE, Strasbourg (FR)

(72) Inventors: Olivier Ludemann-Hombourger, La Wantzenau (FR); Isabelle Martinuzzi, Martigues (FR); Christelle Bobier, Vellinge (SE); Eric Francomme, Vandoeuvre (FR)

(73) Assignee: POLYPEPTIDE LABORATOIRES FRANCE, Strasbourg (FR)

( * ) Notice: Subject to any disclaimer, the term of this patent is extended or adjusted under 35 U.S.C. 154(b) by 0 days.

(21) Appl. No.: 17/046,391

(22) PCT Filed: May 4, 2018

(86) PCT No.: PCT/FR2018/051142
§ 371 (c)(1),
(2) Date: Oct. 9, 2020

(87) PCT Pub. No.: WO2019/211531
PCT Pub. Date: Nov. 7, 2019

(65) Prior Publication Data
US 2021/0094982 A1 Apr. 1, 2021

(51) Int. Cl.
*C07K 1/04* (2006.01)
*B01J 19/24* (2006.01)
(Continued)

(52) U.S. Cl.
CPC ............... *C07K 1/045* (2013.01); *B01J 19/00* (2013.01); *B01J 19/24* (2013.01); *B01J 19/2465* (2013.01);
(Continued)

(58) Field of Classification Search
CPC .... B01J 19/0046; B01J 19/24; B01J 19/0066; B01J 19/2465; B01J 19/1881; C07K 1/045
See application file for complete search history.

(56) References Cited

U.S. PATENT DOCUMENTS 4,746,490 A * 5/1988 Saneii .................. B01J 19/0046
422/111
5,462,748 A * 10/1995 Lloyd .................... C07K 1/045
424/501
(Continued)

FOREIGN PATENT DOCUMENTS

WO        WO 98/34633 A1      8/1998
WO        WO 2012/056300 A2   5/2012
WO        WO 2017/049128 A1   3/2017

OTHER PUBLICATIONS

International Search Report, issued in PCT/FR2018/051142, dated Nov. 8, 2018.
(Continued)

*Primary Examiner* — Lessanework Seifu
(74) *Attorney, Agent, or Firm* — Birch, Stewart, Kolasch & Birch, LLP

(57) ABSTRACT

An automated system of reactors carries out a solid-phase peptide synthesis, and more particularly a solid-phase peptide synthesizer which is automated, by means of a reactor with a liquid-recirculation loop making it possible to measure, in real time, chemical species in the reactor via measuring cells. This system includes inlet pipes, namely: pipes dedicated to the introduction of resin, pipes dedicated to the introduction of the synthesis and washing solvent, pipes dedicated to the introduction of the agent for deprotecting the amino acid introduced, pipes dedicated to the (Continued)

introduction of the reagents, and includes an assembly reactor and a loop for recirculation of the liquid of the reactor.

2 Claims, 7 Drawing Sheets

(51) Int. Cl.
| | |
|---|---|
| *C07K 1/06* | (2006.01) |
| *G01N 21/359* | (2014.01) |
| *G01N 21/65* | (2006.01) |
| *B01J 19/00* | (2006.01) |
| *G01N 21/84* | (2006.01) |

(52) U.S. Cl.
CPC ........... *C07K 1/061* (2013.01); *G01N 21/359* (2013.01); *G01N 21/65* (2013.01); *B01J 2219/24* (2013.01); *G01N 2021/8416* (2013.01)

(56) References Cited

U.S. PATENT DOCUMENTS

| | | | |
|---|---|---|---|
| 6,028,172 A * | 2/2000 | Stepaniuk | ............ B01J 19/0046 530/334 |
| 7,902,488 B2 * | 3/2011 | Collins | .................. C07K 1/045 219/679 |
| 2005/0013738 A1 * | 1/2005 | Schwalbe | ............ G05B 13/024 422/67 |
| 2014/0275481 A1 | 9/2014 | Simon et al. | |
| 2018/0066012 A1 | 3/2018 | Simon et al. | |
| 2019/0329213 A1 * | 10/2019 | Tsukahara | .............. C07K 1/045 |

OTHER PUBLICATIONS

Mäde et al., "Automated solid-phase peptide synthesis to obtain therapeutic peptides", Beilstein J. Org. Chem., 2014, vol. 10, pp. 1197-1212.

* cited by examiner

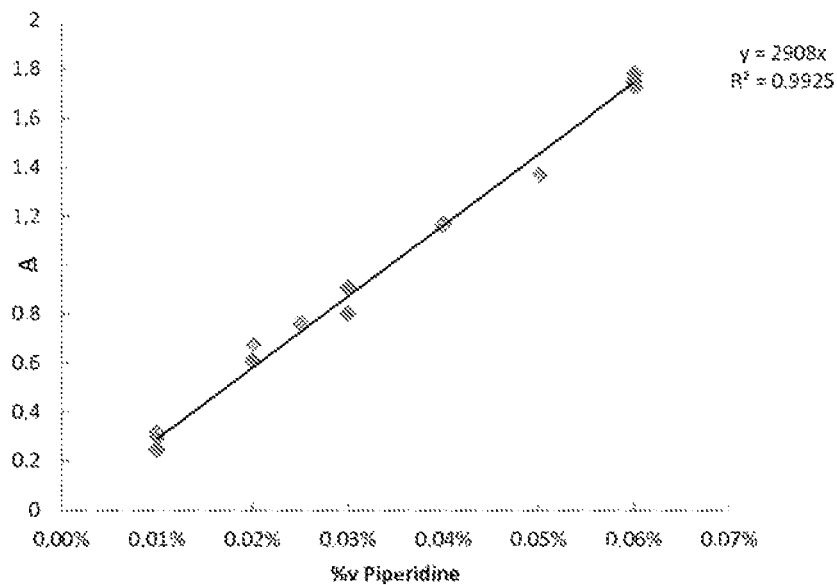
Figure 2. Calibration curve of piperidine by UV spectrometer (390nm)
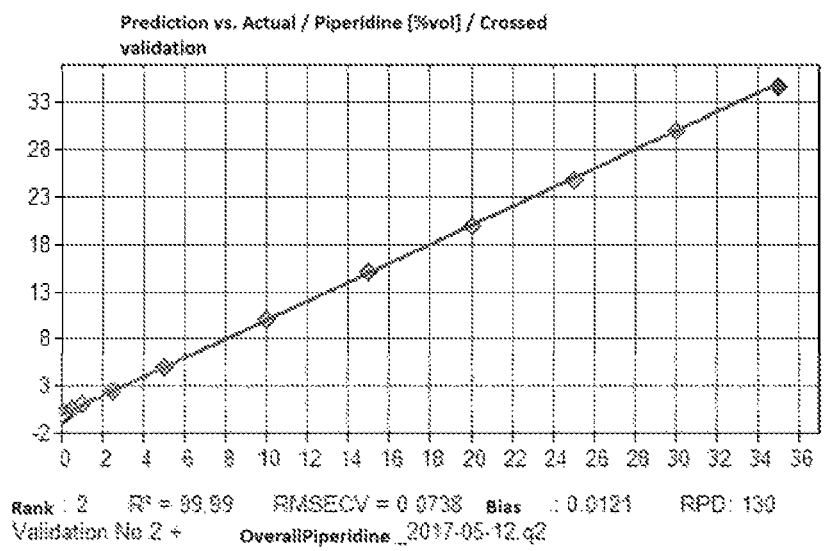
Figure 3. Calibration curve of piperidine between 0.01% and 35%v

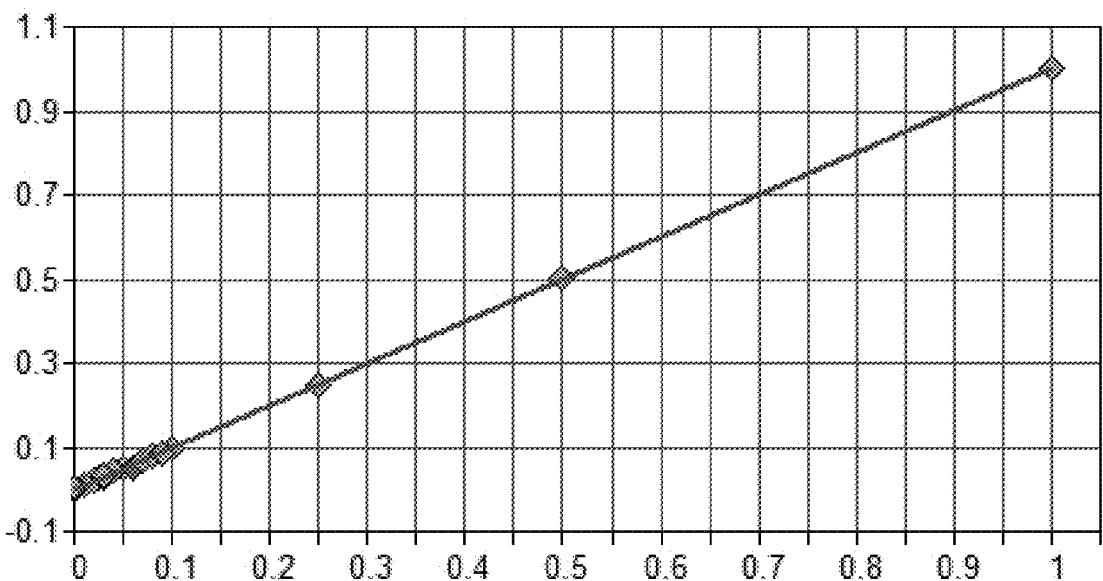
Fig. 4 – Calibration curve of piperidine between 0.01% and 1%v

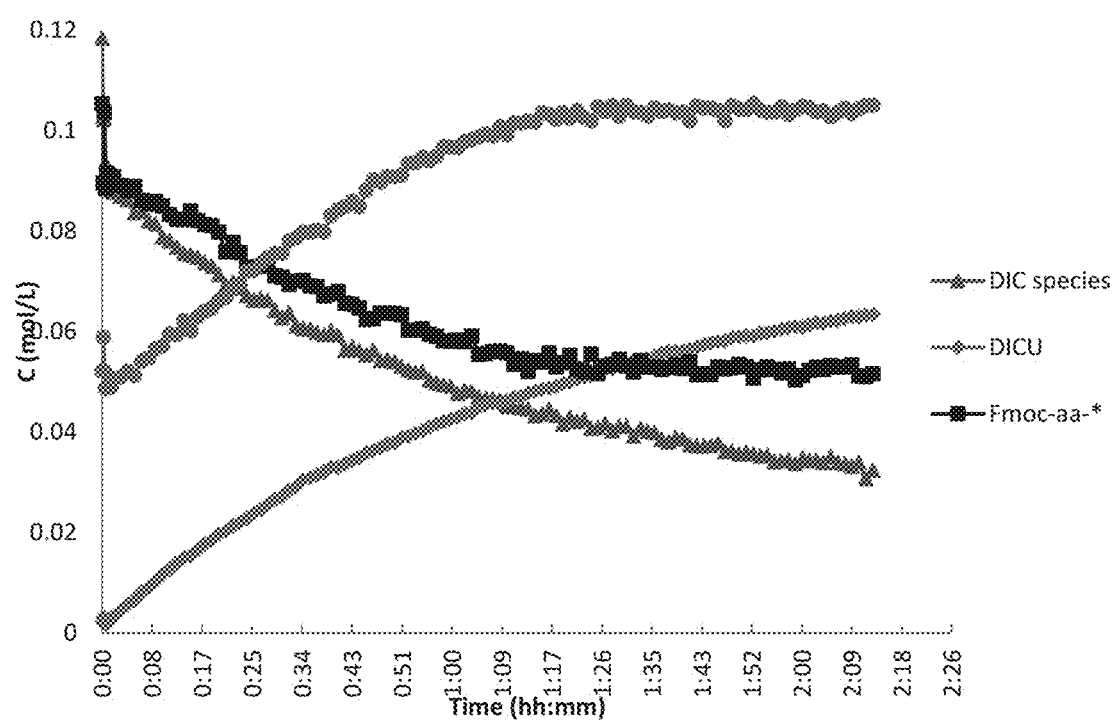
Fig. 5. Evolution of the coupling of histlidine in a peptide resin

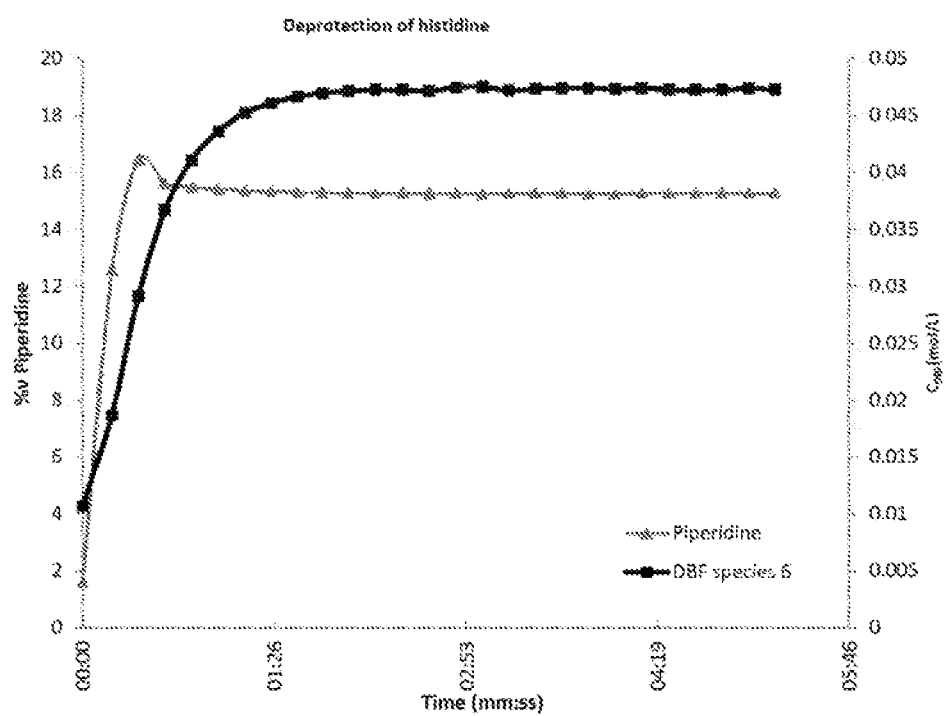
Figure 6. Monitoring of a step of deprotecting histidine

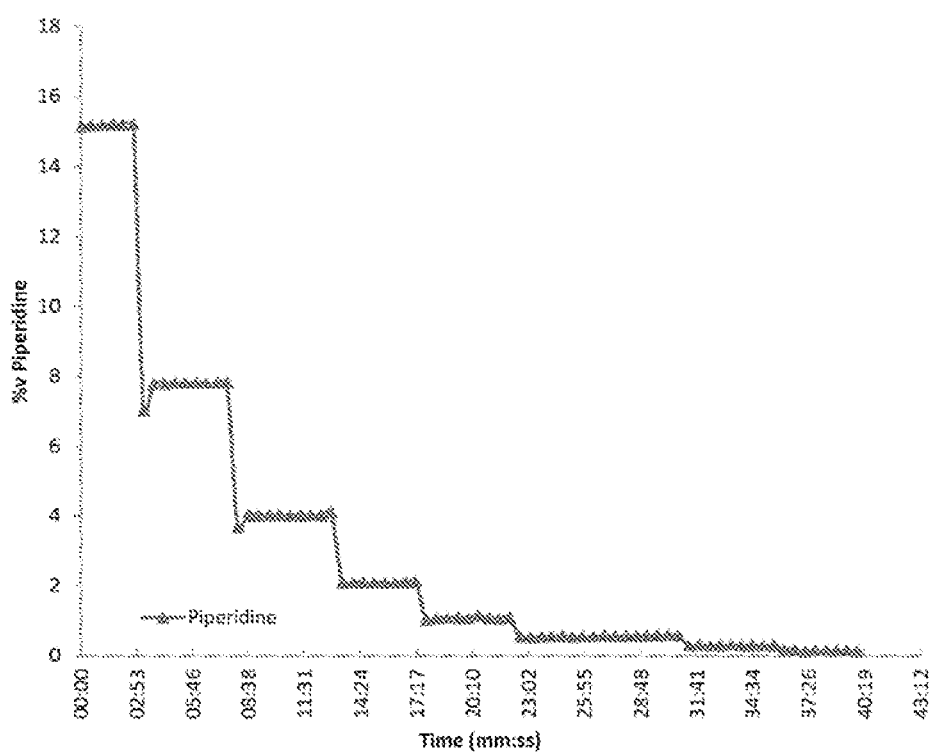
Figure 7. Washings after deprotection of histidine

Disappearance of the deprotection agent over time for a fixed Percolation flow rate

AUTOMATED SYNTHESIS REACTOR SYSTEM WITH A RECIRCULATION LOOP

TECHNICAL FIELD

The present invention relates to an automated reactor system to perform a solid-phase peptide synthesis, and more specifically, a solid-phase peptide synthesizer automated by means of a liquid-recirculation loop reactor making it possible to measure, in real time, chemical species in the reactor via measuring cells.

Peptides are bonded amino acid chains which are the base elements for most living organisms. Consequently, the study of peptides and proteins and the capacity of synthesizing peptides and proteins are of a great interest in biological sciences and medicine.

Solid-phase peptide synthesis emerged in 1963, when R B Merrifield published the synthesis of a sequence constituted of four amino acids by using a solid-phase method (R B MERRIFIELD, Solid Phase Peptide Synthesis I, the synthesis of a tetrapeptide, J. Am. Chem. Soc. 1963, 85 (14), pp 2149-2154).

Since its introduction in 1963 by Merrifield, the solid-phase synthesis has considerably receded the limits of the peptide synthesis known in the homogenous phase. Merrifield had the idea of combining the methodology using activated esters together with the anchoring of the first amino acid on an insoluble polymer matrix. This new synthesis mode therefore made it possible to avoid the undesired reactions since with the immobilization of one of the partners on the solid phase, one single face of an amino acid is available for the coupling. Another advantage of the immobilization of an amino acid on an insoluble polymer is that this enables the use of an excess of reagent in the solution. The excess of reagent is not any longer considered as an impurity for the end product and enables to achieve coupling efficiencies close to 100%. The advantage certainly the most consequent of the solid-phase synthesis, is that all the purification steps between each coupling are removed, since the desired product remains attached to the insoluble polymer, until obtaining the desired peptide. The peptide is then separated from the polymer by chemical cleavage. The progress made by the solid-phase peptide chemistry has contributed to the development of numerous solid supports, as well as to the development of new chemistries for the activation and the protection of amino acids. Currently, two major strategies are used for solid-phase peptide synthesis. These two strategies are based on the use of two types of so-called orthogonal temporary protections Fmoc/Boc, for the protection of the amino function. The main difference between the two types of protective groups is linked to their deprotection mode. The deprotection of the Fmoc group is achieved in a basic medium while the deprotection of the Boc group is achieved in an acidic medium. Currently, the Fmoc/tBu strategy is the most widely used as the final cleavage of the peptide from the solid support uses concentrated TFA (trifluoroacetic acid) while the Boc/Bnl strategy requires the use of concentrated hydrofluoric acid, which is much more dangerous and difficult to handle. Although these two types of protection are deprotected according to two different protocols, the protocol used for the coupling of the different amino acids is similar. The solid-phase peptide synthesis therefore consists of a succession of couplings and deprotections until obtaining the desired peptide which will then be separated from the polymer by chemical cleavage.

During the solid-phase peptide synthesis, the techniques which enables to evaluate the effectiveness of a coupling or a deprotection are based on colorimetric tests which are not quantitative. To be able to analyze the peptide chain quantitively, the molecule must be separated from the solid support to then analyze it with the usual RMN, HPLC and mass spectroscopy techniques. This method, which consists of cleaving the molecule of the support before being able to analyze it, is not satisfactory for purposes of understanding the phenomena which are at the origin of the problems encountered during the synthesis of so-called difficult sequences.

Although mass spectroscopy can offer a high throughput analysis, one of the major drawbacks of using standard spectroscopic methods for the online monitoring is that it requires the solubilization of the sample studied, therefore released from its solid support. The determination of the compound is therefore generally made at the end of the synthesis.

The use of such a cleavage and analysis strategy as means for controlling the quality of the synthesis therefore has several drawbacks. Firstly it is destructive because the samples are consumed, moreover, secondary reactions with cleavage reagents can occur, leading to difficulties in the determination of peptide products by mass spectroscopy due to complicated spectra which are obtained.

Numerous patents in the prior art have attempted to conduct the real-time analysis of ongoing peptide syntheses.

Patent application WO2012056300 protects a a process for real-time monitoring of solid phase peptide synthesis (SPPS) under ambient atmosphere to characterize peptide intermediates or online products. The technical solution described allows to monitor in real time to trace the process of step reactions of the SPPS by use of a light source, an electrospray unit, and a mass spectrometer. However, the use of these analytical techniques have significant disadvantages, namely taking samples dispersed in a solvent which also involves the destruction of said samples, contrary to the method according to the invention. This is referred to as a destructive analysis method. In addition, the solution mentioned is not quantitative and does not enable to know whether the resin is properly washed between the different steps (washing after coupling or washing of the piperidine), but only to know whether the amino acid is coupled on the resin, or also if the amino acid on the resin is deprotected.

Patent application WO 2017049128 describes a system for controlling a solid-phase peptide synthesis by using detectors that allow the reaction to be controlled afterwards by modifying the process, such as removing the reagent. The detectors used measure, in the liquid phase through a detection zone in the system, and one or more signals can be generated corresponding to the fluids. For this purpose, patent WO2017049128 uses an electromagnetic radiation detector placed downstream from a reactor to detect a fluid at the outlet of the reactor, in order to produce a signal. Thus, the parameters can be modulated before or during the solid-phase peptide synthesis reaction process. The disadvantage of this method is that the control is carried out downstream from the reactor, and not in the reactor or in a recirculation loop. In addition, this method monitors the deprotection, but not the coupling and finally, this technique does not allow multi-pass real-time analysis and, contrary to the system according to the invention, this solution implies a large excess of reagents and solvents, which consumes a lot of reagents and is not at all economically viable.

The destructive analytical methods, of colorimetric or spectrophotometric type, have the disadvantage of being irreversible. In addition, they generate modified products and, even more significant, they lower the yield of the final peptide as they are made on resin-peptide aliquots. However, these methods are broadly used as they are rapid and do not require any expensive instrumentation.

Non-destructive analytical methods can also be used in batch processes. For example, the monitoring of reactions by infrared can be mentioned, based on the appearance or the disappearance of functional groups, which can be applied to monitor the solid-phase chemical synthesis, in particular in the field of organic synthesis and to monitor the coupling and deprotection during a peptide synthesis. Infrared and Raman spectroscopies are widely used techniques for the detection and characterization of reaction products as they allow direct analysis of products on solid supports. The development of FT-IR (techniques (Fourier Transform Infra-Red spectroscopy or FT-IR spectroscopy) can also be mentioned, which enables to obtain the infrared absorption spectrum, emission, photoconductivity or Raman diffusion of a solid, liquid or gaseous sample.

Nevertheless, the use of these techniques for solid-phase reactions is limited, in particular due to their high costs and due to them only being able to measure one single position in a sample.

The development of a new system and method for real time non-destructive monitoring and analysis capable of rapidly and simultaneously acquiring information over a large number of samples, but which would also monitor all the reagents in the assembly reactor constitutes a real need, particularly since, unlike existing methods, it would allow total control of the synthesis and a step-by-step monitoring of the solid-phase peptide synthesis for an optimum control of the reaction time, the use of solvents, reagents and a significant cost reduction. In addition, a new real-time detection method would allow to avoid favoring side reactions by stopping the step as soon as the reaction is finished.

The present invention provides such a system and such methods and resolves the limitations mentioned above.

SUMMARY OF THE INVENTION

The invention relates to a reactor system to carry out a solid-phase peptide synthesis, the reactor system comprising: an inlet pipe (1) dedicated to the introduction of resin, an inlet pipe (2) dedicated to the introduction of the synthesis and washing solvent, an inlet pipe (3) dedicated to the introduction of the deprotecting agent of the amino acid supplied, an inlet pipe (4) dedicated to the introduction of reagents, an assembly reactor (9) and a recirculation loop (10) of the liquid of the reactor comprising at least one measuring cell (11) for indirect quantification of the progress of the reaction on the solid phase.

According to a preferred embodiment, the measuring cell (11) is a spectrophotometric measuring cell, and preferably the measuring cell (11) is a cell for measuring by Raman spectroscopy and even more preferably, the measuring cell (11) is a cell for measuring near-infrared.

Near-infrared spectroscopy, also called NIR spectroscopy is a quantitative and qualitative analysis technique used in chemistry. The technique uses a spectrum extending to wavelengths of 700-2500 nm ($\lambda$), i.e. between the wave numbers 14286 and 4000 cm$^{-1}$ ($\nu$).

According to another preferred embodiment, the reactor system for performing a solid-phase peptide synthesis further comprises in the assembly reactor (9), a filtration system.

A filtration system according to the invention is advantageously a filtration system made from sintered stainless steel material and/or a sintering sheet.

According to another preferred embodiment, the reactor system for performing a solid-phase peptide synthesis further comprises a reactor (5) for pre-activating amino acids and/or dissolving powders and an inlet (6) connecting the reactor (5) to the assembly reactor (9).

According to a preferred embodiment, the reactor system for performing a solid-phase peptide synthesis further comprises an inlet pipe of additional solvent (7) and an inlet pipe of additional reagent (8) on the pre-activation reactor (5).

According to another preferred embodiment, the reactor system for performing a solid-phase peptide synthesis further comprises, in the recirculation loop (10), at least one cell for measuring conductivity.

According to another preferred embodiment, the reactor system for performing a solid-phase peptide synthesis further comprises, in the recirculation loop (10), at least one cell for measuring the ultraviolet absorbance.

According to another preferred embodiment, the reactor system for performing a solid-phase peptide synthesis further comprises, in the recirculation loop (10), a cell for measuring by Raman spectroscopy.

These measuring cells can be additional to the measuring cells already present in the recirculation loop.

According to a preferred embodiment, the reactor system for performing a solid-phase peptide synthesis further comprises a self-priming pump at the level of the inlet pipe (7) dedicated to the introduction of the synthesis solvent.

According to another preferred embodiment, the reactor system for performing a solid-phase peptide synthesis further comprises a level sensor for measuring the level of resins and/or liquid in the reactor.

The level sensor enables the continuous measuring of level of liquids present in the reactor and thus to have a monitoring in real time of the washing to optimize its effectiveness and to reduce the volume of solvent used.

According to another preferred embodiment, the reactor system for achieving a solid-phase peptide synthesis further comprises, in the assembly reactor (9), a pressure sensor.

According to another preferred embodiment, the reactor system for achieving a solid-phase peptide synthesis further comprises in the assembly reactor (9), a conductivity cell at the bottom of the reactor.

According to another preferred embodiment, the reactor system for achieving a solid-phase peptide synthesis further comprises, in the assembly reactor (9), a cell for measuring the pH at the bottom of the reactor.

According to another preferred embodiment, the reactor system for achieving a solid-phase peptide synthesis further comprises a device for dispersing the solvent situated at the end of the line, at the level of the reactor (9).

Another aspect of the invention is a solid-phase peptide synthesis process comprising the following steps:

a) Coupling by stirring in an assembly reactor and starting the recirculation loop, b) Real-time monitoring of the coupling step by the measure of a detector in a recirculation loop for quantifying the chemical species of the mixture, c) Washing of the assembly reactor, d) Deprotection by introducing a synthetic solvent and a deprotection agent into the reactor and initiating stirring in the reactor and in the recirculation loop, e) Real-time monitoring of the deprotection step in the reactor by the measure of a detector, f) Washing of the deprotection agent, g) Real-time monitoring of the washing step (f) of the concentration of the deprotection agent in the reactor by the measure of a detector.

According to a preferred embodiment of the invention, before the coupling step in the assembly reactor, the method comprises a preliminary step of pre-activating the amino acid in a dissolution reactor, the monitoring in real time of the pre-activation step in the reactor by measurement from a detector, the introduction of the pre-activated mixture in the assembly reactor.

According to a preferred embodiment of the invention, the monitoring in real time of the coupling step is done by the measure of a detector selected from among a near-infrared detector, a conductimeter, a UV detector, a Raman spectroscopy detector and/or a pH detector.

According to a preferred embodiment of the invention, the real-time monitoring of the pre-activation step is carried out by a conductivity meter, a UV detector, a Raman spectroscopy detector and/or a pH detector.

According to a preferred embodiment of the invention, the real-time monitoring of the washing step is done by the measure of a detector selected from among a near-infrared detector, a conductivity meter, a UV detector, a Raman spectroscopy detector and/or a pH detector.

According to a preferred embodiment of the invention, the real-time monitoring of the pre-activation step is done by the measure of a detector selected from among a near-infrared detector, a conductivity meter, a UV detector, a Raman spectroscopy detector and/or a pH detector.

According to a preferred embodiment of the invention, the washing in step (i) is done by percolation.

According to a preferred embodiment of the invention, the percolation is done with a level control by way of a radar-type sensor.

According to another preferred embodiment of the invention, the concentration of the deprotection agent is measured in real time at the reactor outlet. This measuring is done during the percolation to monitor its development and stop the introduction of the solvent and finish the draining.

Another aspect of the invention is the use of a level sensor to determine the height of the liquid in the reactor with respect to the height of the resin bed for a percolation step in order to optimize in real time the washing and to minimize the solvent consumption.

Another aspect of the invention is the use of a percolation system in a process for monitoring in real time according to the invention for the filtration of a solvent. The monitoring in real time during the use of a percolation system is done by way of a sensor, in particular a radar-type sensor, thus making it possible to monitor the reaction and the control of quantities of solvents and reagents in real time to limit the costs of it.

The invention also relates to a method and a process for monitoring in real time, a chemical reaction comprising a reactor system according to the invention, a control unit (13) controlled by software enabling the automation of the reactor system, thanks to the advanced online control in an assembly reactor and in a recirculation loop. This method for monitoring in real time is advantageously used for peptide synthesis reactions, more preferably the solid-phase peptide synthesis.

Advantageously, the invention is a device comprising computerized means for the implementation of the method of the invention. According to another of its aspects, the method according to the invention is at least partially implemented by computerized means foreseen in the system according to the invention.

The command system (13) comprises a control unit of the reactor system according to the invention. This unit is advantageously embedded on the system according to the invention. More preferably, this control unit includes a fixed computerized terminal (for example, a PC, a Macintosh or a Unix system) and/or mobile (for example, of smartphone/tablet type) provided with one or more items of software/applications adapted to allow the automatic management of the control of the system according to the invention using the data provided by the different sensors. Thus, as soon as the measuring cells, or also sensors, of the peptide synthesis system according to the invention is switched on and receives data from different sensors, the software/application triggers control signals within the electronic unit and the stopping or not of the current step.

Without this being limiting, said adapted software/applications of the system according to the invention can also collect information on the nature and the quantity of the reagents and solvents used for the peptide synthesis, for the purpose of managing stocks of said reagents and solvents. The integration by these adapted items of software/applications over a given future period, can enable to integrate a provisional element for holding stocks of reagents and solvents at levels required to guarantee a good progress of all of the synthesis steps in the desired time, but not financially disadvantageous.

According to the present invention, measuring cells and sensors are referred to equally. For example, an infrared sensor or an infrared measuring cell is an infrared detection device which detects the infrared wavelengths.

The device and the method of the invention has numerous advantages with respect to the already-existing solutions.

The use of a reactor with an advanced online control within it, and/or in the circulation loop enables to monitor each step of the reaction, in order to know precisely when the step has ended. With this system, a significant saving of time is obtained. In addition, operators are also less exposed to dangerous reagents, as less samples must be sampled. A reactor system and a synthesis method according to the invention also enables to stop the reaction as soon as it is ended by limiting the secondary reactions and to optimize the purity of the synthesized peptide.

The monitoring can also be carried out thanks to the conductivity and the temperature in addition to the near-infrared sensors even inside the reactor but it will be preferably carried out over the liquid phase because, thanks to the recirculation loop on the reactor, numerous sensors can be placed in addition to that of FTNIR (Fourier Transform Near-Infrared Spectroscopy), such as sensors for measuring conductivity and UV.

Another advantage of the system and of the method according to the invention is that one single calibration is used for all the Fmoc protected natural amino acids. The system and the method according to the invention also enable to precisely quantify the deprotection agent and the release of dibenzofulvenes during steps of deprotecting Fmoc protected amino acids in order to know when the reaction has ended.

The system and the method according to the invention also enable to monitor the washing and the decrease of concentrations of reagents up to a threshold, in order to know when the washing is completed. Thanks to this advanced online control, it is possible, not only to monitor the development of the reactions, but also to use it for the automatisation.

According to a preferred embodiment of the invention, it is possible to select which measuring cells will determine the end of a step when a threshold is reached or when the stabilization is established. Thus, the reactor can operate automatically for a few steps according to the online monitoring results.

Thanks to a radar-type sensor, capable of determining the height of the liquid in the reactor, with respect to the height of the resin bed and thanks to the monitoring in the recirculation loop, the reactor can operate automatically and thus lead to a more effective washing of the resin, by operating according to a percolation mode.

Advantageously, the system and the method according to the invention uses a percolation process to wash the solvent and to optimize the online monitoring by the quantity of the reagents and solvents used.

According to a preferred embodiment of the invention, when a unit or a percolation process is used, the liquid is introduced by the top of the reactor on the resin at the same flow rate as the outlet flow rate of the reactor, thanks to the control of the height of the liquid which must remain constant in the reactor for all the washing.

This washing mode comprises a filled resin bed and a distribution system for the inlet of the liquid at the top of the reactor for a good distribution of the liquid on the surface of the resin. This washing mode is the most effective and enables a significant reduction of the consumption of solvent with respect to the other existing modes. The reactor is also controlled in temperature in order to be able to change temperature between two different steps in a few minutes.

The present invention reduces the cost required for purchasing starting products and treating the residual liquid, by considerably reducing the quantity of reagents, solvents actually consumed and the waste liquid (organic solvent), damaging for the environment.

DESCRIPTION OF THE FIGURES

The present invention will be better understood from the detailed description below and the appended drawings which are given as an illustration, and therefore, are not limiting of the present invention, and wherein.

Figure 1:
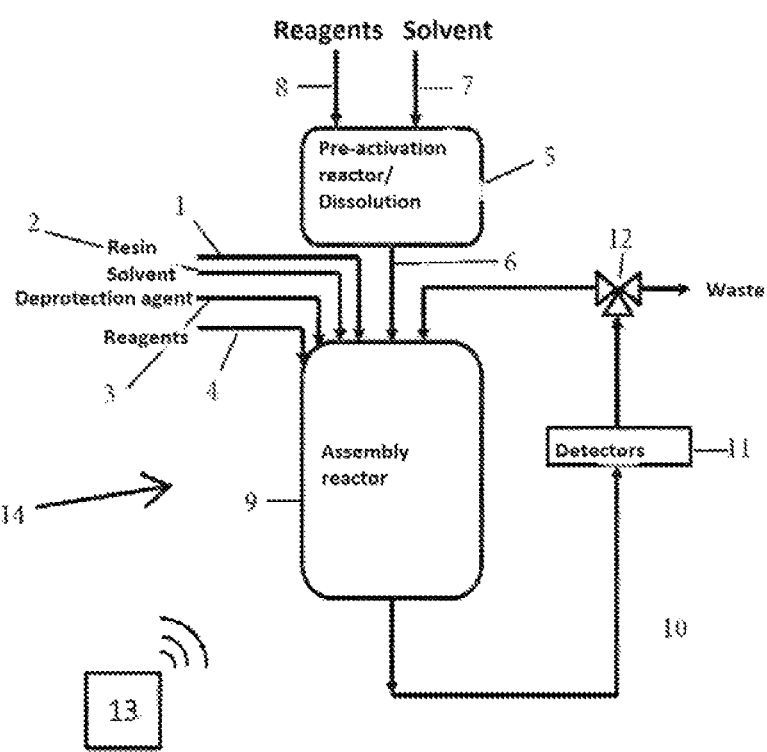
FIG. 1 is a schematic view showing a synthesis reactor system (14) to achieve a solid-phase peptide synthesis with a liquid-recirculation loop (10) of the reactor making it possible to measure in real time, the evolution of the chemical species in the peptide automatic synthesizer of the present invention.

The numeric references of FIG. 1 designate the following elements: An inlet pipe dedicated to the introduction of the resin (1), an inlet pipe dedicated to the introduction of the synthesis solvent (2), optionally introduced by a self-priming pump. According to a preferred embodiment, a pre-activation reactor (5) of the amino acids and/or dissolution of the powders and connected to the assembly reactor (9) by an inlet pipe (6), an inlet pipe dedicated to the introduction of the deprotection agent of the amino acid (3) introduced by a self-priming pump and an inlet pipe dedicated to the introduction of the solvent (4) are connected to the assembly reactor (9), an additional inlet pipe dedicated to the introduction of reagents (8) and an inlet pipe dedicated to the introduction of the solvent are connected to the pre-activation reactor (5). The liquid-recirculation loop (10) of the reactor comprising at least one detector (11), preferably a near-infrared spectrophotometric measuring cell, a command module (13) controlled by a software making it possible for the automatisation of the reactor system, thanks to the advanced online control in the recirculation loop. A three-way valve (12) at the outlet of the sensors on the recirculation loop of the assembly reactor (9) enables, according to the needs, to pass into draining mode or not.

FIG. 2 represents a calibration curve of the piperidine by UV (390 nm) for the quantification by infrared.

FIG. 3 represents the calibration curve of the piperidine between 0.01% and 35% v.

FIG. 4 represents the calibration curve of the piperidine between 0.01% and 1% v.

FIG. 5 represents the monitoring in the liquid phase and over time of the coupling of histidine on a peptide-resin. Observation of the disappearance of the reagents and the formation of a product (DICU).

FIG. 6 represents the monitoring of a deprotection step of histidine.

FIG. 7 represents the washings of the piperidine after deprotection of histidine.

Figure 8:
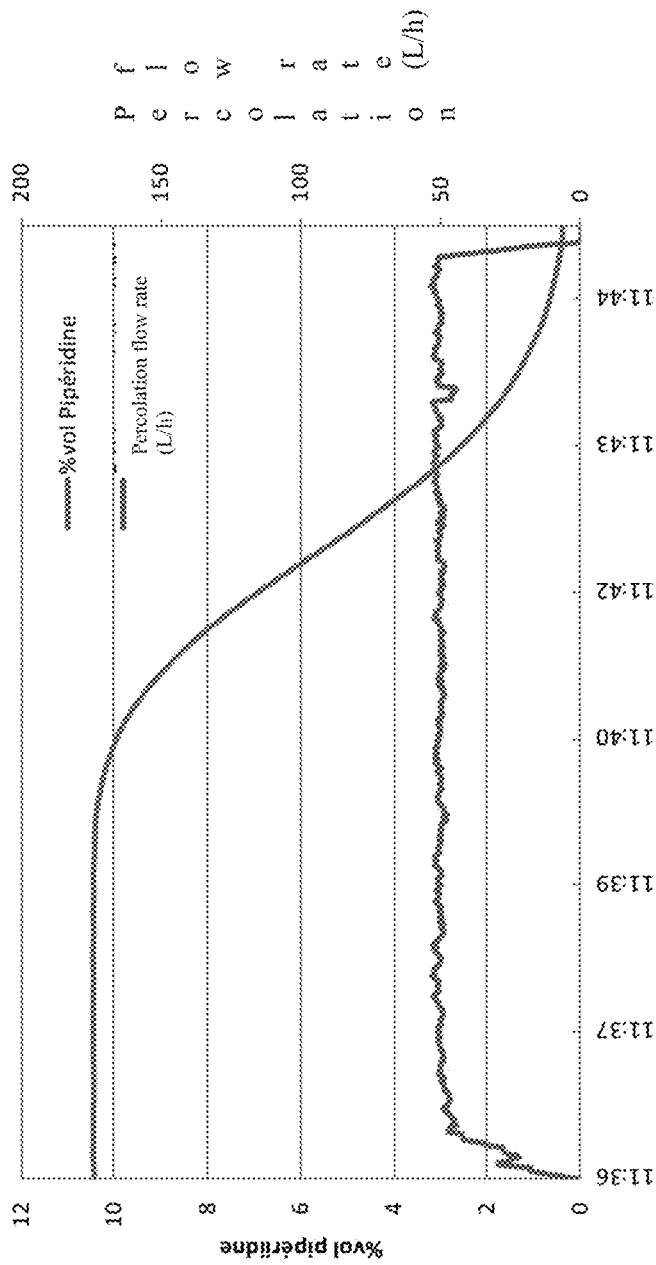

FIG. 8 represents the disappearance of the deprotection agent over time for a fixed percolation flow rate.

DETAILED DESCRIPTION

Below, preferred embodiments and implementations of the system and of the method according to the invention are described. This description is made also in reference to the appended figures.

The synthesis reactor is a stainless steel reactor with a capacity of 25 litres. A filtration device is placed at the bottom of the reactor in order to retain the resin and discharge the solvents. This filtration device is formed of a sintered stainless steel material but, could consist of a filtering sheet or any other filtration system known to a person skilled in the art.

The reactor has a stirring blade in order to mix, as best as possible, the resin and the liquid. This stirring blade can rotate in both rotating directions. On the top of the reactor, several inlets are present, of which one inlet is dedicated to the introduction of the resin and one inlet is dedicated to the introduction of the synthesis solvent (DMF), synthesis solvent, introduced by a self-priming pump. The introduction flow rate, as well as the volume introduced are measured and quantified by a mass flow sensor. The flow rates can range from 35 l/h to 600 l/h. The solvent can be heated or cooled as needed before entry into the reactor via a heat exchanger. In order to clean the reactor correctly between each step of the synthesis, a device for dispersing the solvent is located at the end of the line, at the level of the reactor. This device operates correctly between 20 and 1000 l/h. An inlet pipe dedicated to the introduction of the agent for deprotecting the amino acid can also be placed on the top of the assembly reactor. It is done thanks to a self-priming pump, of which the flow rate is 20 to 1000 l/h. The introduction flow rate, as well as the volume introduced are measured and quantified by a mass flow sensor. The deprotection agent can be premixed or not with the synthesis solvent before introduction into the reactor. An inlet pipe for additional solvent, of which the volume and the flow rate are controlled by a mass flow sensor, can also be placed at the top of the assembly reactor.

According to an embodiment of the invention, a nitrogen inlet pipe, with the aim of making the reactor inert or of flushing by nitrogen the reactor, is placed on the top of the assembly reactor.

According to another embodiment of the invention, the assembly reactor can be equipped with different sensors:
  A near-infrared spectroscopy sensor,
  A level sensor (of radar-type), to measure the resin or liquid level in the reactor, A pressure sensor, A conductivity cell at the bottom of the reactor to measure the conductivity at any moment of the synthesis in the solid-liquid phase, A pH-meter at the bottom of the reactor to measure the pH at any moment of the synthesis in the solid-liquid phase.

A liquid-recirculation loop of the assembly reactor enables a real-time measurement of the evolution of the chemical species in the reactor via measuring cells which are, a conductivity cell, a near-infrared cell (from 1 mm to 30 mm of optical path) and a UV cell (from 0.5 mm to 10 mm of optical path). For a given step, the flow of the liquid into the loop occurs numerous times and the flow rate of the recirculation can be adjusted according to the steps, if the reactions are slow or rapid.

When a step is finished, the liquid from the reactor is drained via the sintered material, by passing through the measuring cells of the recirculation loop, which can thus give information about the liquid phase at the outlet of the reactor.

According to an embodiment of the invention, the assembly reactor is connected to another reactor which could be used to dissolve powders or to pre-activate the amino acids before introduction into the reactor. This reactor is a glass double-envelope reactor with a capacity of 10 l. It is provided with a stirrer making it possible to dissolve powders. It optionally has a conductivity probe and a pressure sensor. There is an inlet on the top, in order to introduce the powders. An inlet pipe for solvent enables, as for the assembly reactor, to introduce the solvent, thanks to a self-priming pump, ranging between 20 and 1000 l/h. The flow rate and the introduction volume are measured by a mass flow sensor. A last inlet pipe is present to introduce a solvent or a coupling agent.

The assembly is controlled by a software making it possible for the automation of the installation thanks to the advanced online control.

Example 1. Operation of the Installation

During a solid-phase synthesis, this starts by introducing the resin into the reactor via the dedicated inlet. A predefined volume of synthesis solvent is added at a predefined flow rate via the dedicated inlet. The resin-solvent mixture is stirred, then, once the resin is inflated, the solvent is drained via the outlet at the reactor bottom. The operation is restarted several times. At the same time, the amino acid or the linker is dissolved/or pre-activated in the dissolution reactor in the DMF. This is stirred. Either the coupling agent is added or not. If so, the pre-activation step is followed, preferably thanks to a conductivity cell.

Once the pre-activation is finished, the mixture is introduced in the assembly reactor. The stirring is started in the assembly reactor and the recirculation loop is started. The infrared measuring in the recirculation loop enables to quantify the chemical species of the mixture. The concentration of the reagents decrease and those of the sub-products of the reaction increase in the liquid phase until a stabilization. Once the stabilization is reached, the step is finished, then the assembly reactor is drained via the recirculation loop which, thanks to a three-way valve at the outlet of the sensors, enables to pass into draining mode.

With the coupling step being finished, the synthesis solvent is introduced in the reactor at a predefined volume and flow rate. The solvent-resin mixture is stirred and the recirculation loop is started. When the signals of conductivities are stable in the reactor, and/or the signals in the recirculation loop, the draining of the reactor is started. This step is carried out several times, preferably at least three times until reaching the desired residual concentrations in the reactor.

Once this step of washing the resin is finished, the deprotection step starts. The synthesis solvent and the deprotection agent are introduced in the reactor via the dedicated inlet pipes. The stirring in the reactor is then started, as well as the recirculation loop. In real time, the deprotection step is monitored in the reactor thanks to the online measuring cells.

The conductivity increases in the reactor up to a stabilization indicating the end of the reaction. The quantification of the species in the reactor can be done, preferably, thanks to an infrared cell. In this case, the monitoring of the formation of the dibenzofulvene and the consumption of the deprotection agent, here piperidine, is possible.

The increase of the UV absorbance reveals the formation of the dibenzofulvene and its stabilization indicates the end of the deprotection step. The quantification of this species by UV can be done if a stabilization of the UV is not sufficient for interpreting the signals.

Once the step has finished, a draining of the reactor occurs. A step of washing the deprotection agent ensues. This washing step can be done in two ways.

According to an embodiment of the invention, the washing step is carried out in successive batches of introducing the washing solvent, here the DMF, stirring and recirculation loop, then draining. In each batch, an infrared cell measures the concentration of piperidine in the reactor. When the infrared measurement gives the piperidine threshold reached, a last draining is carried out.

According to another preferred embodiment, the washing step can also be done, and surprisingly, by percolation thanks to a system comprising:

A distribution of homogenous washing solvent on the resin bed,

A measuring of the level of liquid and an adjustment of the flow rate based on the measurement of level of liquid by a suitable sensor.

The optimization of the volumes of washing with DMF is achieved. The flow rate of introducing the DMF is equal, preferably, to the draining flow rate of the reactor thus keeping the constant level of liquid within the reactor, and closest to the level of the resin bed. The measuring of concentration of the deprotection agent, for example piperidine, is measured in real time at the outlet of the reactor. Once the threshold of the deprotection agent is reached, the introduction of the washing solvent is stopped and the draining is finished.

Once the resin is washed, the same steps are restarted up to the end of the assembly of the peptide namely, pre-activation or dissolution of the amino acids, coupling of the amino acid on the resin, washing of the resin, deprotecting of the amino acid, washing of the resin.

The use of a recirculation loop on the assembly reactor comprising a measuring cell, in particular near-infrared, has numerous advantages with respect to the solutions of the prior art. In particular, the following chemical species can be quantified, directly and non-indirectly, according to the step wherein the assembly of the peptide is found.

During the coupling and washing after coupling, the system enables to quantify the amino acids protected by an Fmoc-type group (Fmoc-aa) whatever their activation status, Fmoc-aa-OH, Fmoc-aa-OBt, Fmoc-aa-Oxyma or Fmoc-aa-DIC and valid whatever the amino acid, in the presence or not of HOBt, Oxyma, DIC, DICU, or water, diisopropylurea (DICU) in the presence of the coupling agents, for example HOBt, Oxyma, DIC, Fmoc-aa, the sum of HOBt (1-hydroxybenzotriazole)+Fmoc-aa-OBt in the presence of DIC, DICU and Fmoc-aa; the sum of Oxyma+Fmoc-aa-oxyma in the presence of DIC, DICU and Fmoc-aa; the sum of DIC (N,N'-diisopropylcarbodiimide)+Fmoc-aa-DIC.

The evolution can also be monitored, without quantification if needed, of all species present or not (creation, disappearance or stabilization of the concentration of species) in the presence of other coupling agents in the medium: DIC (N'N'-diisopropylcarbodiimide)+Fmoc-aa-OH, Fmoc-aa-Obt, Fmoc-aa-Oxyma, Fmoc-aa-DIC.

Calibration of Piperidine for Quantification By Infrared

A calibration curve must be made before being able to create a method of quantification by infrared.

The inventors have selected to arbitrarily use an already-existing quantification method which is well-known to a person skilled in the art for piperidine, namely a method of quantification by UV spectrometer.

It is an indirect method where piperidine in the DMF is derivatised with DNFB then analyzed by UV spectrometry at 390 nm after 30 minutes of derivatisation. As a non-limiting example, a spectrophotometer usable according to the invention is that of the company Thermo Scientific of reference Genesys 10S UV-Vis.

After 30 minutes of derivatisation, the concentration of piperidine is measured at 390 nm.

The calibration curve of piperidine is represented in FIG. 2.

Once the calibration curve on UV is achieved, samples of piperidine are prepared at different concentrations known between 0.01% and 35% by volume of piperidine in the DMF. To have an increased precision for low values of piperidine, numerous samples have been prepared between 0.01% and 1% of piperidine.

These samples have then been passed in the measuring cell of the infrared spectrometer (Manufacturer Bruker under the commercial reference Matrix-F) identical or not, to that of the system according to the invention.

In order to have a method for correct quantification of piperidine by infrared, real samples must also be passed over the cell, i.e. samples coming from steps of deprotection and washing after deprotection. These contain, in particular, dibenzofulvenes, reagent traces (Fmoc-aa, DIC, DICU, HOBt, Oxyma) in addition to piperidine in the DMF.

As quantification by infrared is a quantification based on spectral bands and not a highly precise wavelength, it is useful during the calibration, to have samples close to real synthesis solutions.

The near-infrared quantification is a multivariable calibration making use of a matrix resolution and statistical methods. These methods are directly integrated with the software for controlling the infrared spectrometer.

Real samples of deprotection and washing after deprotection have been passed over the infrared cell and have been analyzed at the same by UV spectrometry in order to determine the real concentration of piperidine in the samples.

Once the samples have passed over the NIR (NEAR-INFRARED) cell at known concentrations of piperidine, the multivariable analysis can start and determine the best quantification method proposed by the software. This method must then be tested and proven by passing other samples at known concentrations and see if the calibration curve proposed actually enables to quantify the piperidine in the desired margin of error.

In the case of piperidine, two calibration curves have been produced as the measuring range is very broad (0.01% to 35% of piperidine) and that the precision with a low piperidine content must be important.

Samples at known concentrations of piperidine have been analyzed by the infrared quantification method.

FIG. 3 represents the calibration curve where samples at known concentrations of piperidine have been analyzed by the infrared quantification method between 0.01% and 35% of piperidine.

FIG. 4 represents the calibration curve of piperidine between 0.01% and 1% of piperidine.

The results enable to validate the calibration curves of piperidine by infrared.

Monitoring Different Species Present in the System

The invention proposes a non-limiting example of monitoring and of quantifications by infrared of the different species during different steps of the peptide synthesis.

Monitoring of a Step of Coupling an Histidine on a Given Peptide-Resin

The amino acid and the HOBT are dissolved in the dissolution reactor. They are then introduced in the assembly reactor, as well as the DIC. The stirring is started and the recirculation loop is started up.

The infrared analysis over time can be seen in FIG. 7.

The stabilization of the signals occurs after around 2 hours. The final concentration of the species and in particular, Fmoc-aa-* (corresponding to histidine), is close to the expected concentration. The coupling is finished. The draining of the reactor can occur.

DMF is introduced in the assembly reactor. The stirring is thus started and the recirculation loop is started up. Thus, the quantity of piperidine necessary for the deprotection is added. The measuring of the signals by infrared in the recirculation loop can be seen in FIG. 8.

This shows a consumption of piperidine and a release of dibenzofulvenes in the assembly reactor. The deprotection occurs. Once the stabilization of the signals is observed, the reaction no longer develops. The reactor is then drained.

Once the deprotections are finished, the evolution of the concentration of piperidine can be monitored during the batch washing.

The results are presented in FIG. 9.

For this, a predefined quantity of DMF is introduced in the assembly reactor. The stirring is started, as well as the recirculation loop. By infrared measuring, the quantity of piperidine present in the reactor is quantified. At each stabilization of the concentration of piperidine, the reactor is drained. As long as the obtained value of piperidine is not sufficiently low, a washing is restarted until obtaining the desired concentration.

Optimization of the Washing Time of the System By Percolation

According to a preferred embodiment of the invention, the chemical synthesis reactor system is connected to a percolation system, in order to also optimize the washing time and the quantities of washing solvent used.

In the sense of the present invention, percolation means that the solvent, in particular washing solvent, is passed through a fixed bed, such as a resin to carry out an extraction.

The percolation is carried out on a resin, for example a 4-methylbenzhydrylamine hydrochloride resin or any other resin known by a person skilled in the art (to be confirmed or give another example), simply deposited on a fixed bed on the filtration system and distributed homogenously and horizontally on its surface in order to avoid any preferably path of the washing solvent through the resin bed.

The washing solvent, such as DMF, is introduced thanks to a distribution system which enables to avoid disturbing the resin bed, such that it remains horizontal on its surface.

The liquid level above the resin is controlled as close as possible to the resin bed without disturbing it, in order to decrease the quantity of washing solvent used by limiting the remixing phenomena.

The washing solvent flow rate is optimized thanks to the determination of the transfer kinetics of the species to be removed between the solid phase (resin) and the liquid phase (washing solvent).

Thus, an excessively high flow rate would not enable for the species to diffuse and would involve an overconsumption of the washing solvent and a flow rate which is excessively low would enable for the species to diffuse, but would involve a washing time which is too long.

The following example shows that according to the washing flow rate, the effectiveness of the washings is not the same.

The experiment is carried out in a glass reactor of 10 cm in diameter equipped with a sintered material containing a resin bed, 10 cm high, on which a peptide is coupled. It is sought to reduce the concentration of the deprotection agent by carrying out a percolation with the washing solvent. The resin bed is homogenous and horizontal, there is no preferential path and the washing solvent is distributed such that the resin bed remains horizontal on the surface.

In the following table, the impact of the washing solvent on the effectiveness of washing by percolation can be seen.

| Washing solvent flow rate (ml/min) | ml of washing solvent | Washing time (min) |
|---|---|---|
| 50 | 930 | 20 |
| 80 | 1000 | 12 |
| 190 | 1050 | 6 |
| 300 | 1200 | 4 |

At 50 ml/min of percolation flow rate, to reach an optimum washing, 930 ml of washing solvent is needed, that is 20 minutes of washing as a maximum.

At 300 ml/min of percolation flow rate, to reach the same optimum washing, 1200 ml of washing solvent is needed (+20% of additional solvent with respect to a flow rate of 50 ml/min), that is 4 minutes of washing (−79% of time with respect to a flow rate of 50 l/h).

It is seen that at a flow rate that is excessively high, more washing solvent is needed to reach the same washing threshold, but a shorter washing time.

Results of the Percolation on the System According to the Invention

The following example shows a washing by percolation on the reactor of the invention with a resin bed height of 5.6 cm.

An online analysis on the recirculation loop enables to precisely quantify the removal of the deprotection agent, here piperidine.

FIG. 8 shows the disappearance of the deprotection agent over time for a fixed percolation flow rate.

The present invention thus being described, it is clear that the same thing can be modified in numerous ways. Such variations must not be considered as a departure from the sense and scope of the invention, and all the modifications which would be clear for a person skilled in the art are intended to be included in the scope of the following claims.

The invention claimed is:

1. A reactor system for performing a solid-phase peptide synthesis, the reactor system comprising:
   an inlet pipe dedicated to the introduction of resin;
   an inlet pipe dedicated to the introduction of a synthesis and washing solvent;
   an inlet pipe dedicated to the introduction of a deprotecting agent of an amino acid supplied;
   an inlet pipe dedicated to the introduction of reagents;
   an assembly reactor;
   a recirculation loop of a liquid in the assembly reactor comprising at least one measuring cell for indirect quantification of the progress of the reaction on the solid phase; and
   a level sensor to determine a height of the liquid in the assembly reactor with respect to a height of a bed of the resin.

2. The reactor system for performing a solid-phase peptide synthesis according to claim 1, wherein the level sensor is a radar sensor.

* * * * *